United States Patent [19]

Vulliens et al.

[11] 4,363,235

[45] Dec. 14, 1982

[54] SAMPLING APPARATUS FOR A PRODUCTION LINE

[75] Inventors: Philippe Vulliens, Palezieux; Guy Siggen, Juriens, both of Switzerland

[73] Assignee: Baumgartner Papiers S.A., Switzerland

[21] Appl. No.: 199,235

[22] Filed: Oct. 21, 1980

[30] Foreign Application Priority Data

Jan. 24, 1980 [CH] Switzerland ............................ 557/80

[51] Int. Cl.³ ............................................ G01N 15/08
[52] U.S. Cl. ........................................ 73/38; 198/488; 198/689; 209/535; 209/537
[58] Field of Search ................ 198/471, 480, 485–490, 198/689; 131/94, 88; 73/38, 37.8; 209/535–537, 591, 643

[56] References Cited

U.S. PATENT DOCUMENTS

2,917,156 12/1959 Pollmann ............................ 198/488
3,094,128 6/1963 Dearsley ........................ 198/689 X

*Primary Examiner*—John J. Love
*Assistant Examiner*—Douglas D. Watts
*Attorney, Agent, or Firm*—Kane, Dalsimer, Kane, Sullivan and Kurucz

[57] ABSTRACT

Apparatus for the automatic removal of a sample from a production line comprises a rotary removal arm connected to a vacuum source for bringing the sample into a position opposite a diametral bore in a rotary disc. The disc is intended to bring the sample into a transfer position. The disc may be associated with devices for checking the pressure drop and weight of the sample. The sample may be reintroduced back into the production line.

9 Claims, 6 Drawing Figures

Fig. 6
Fig. 5
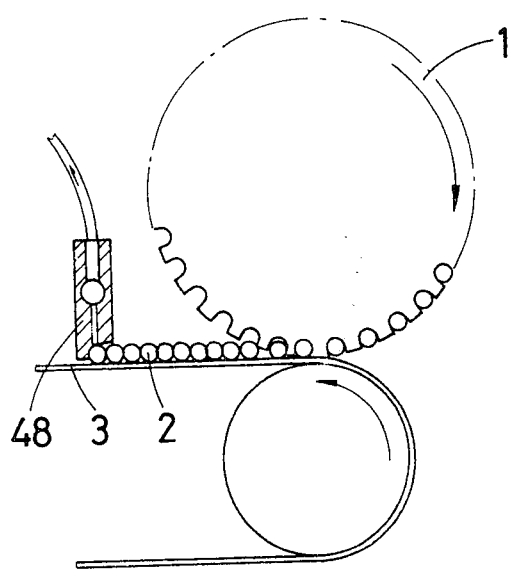
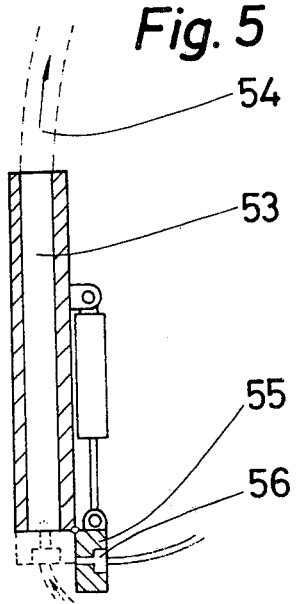
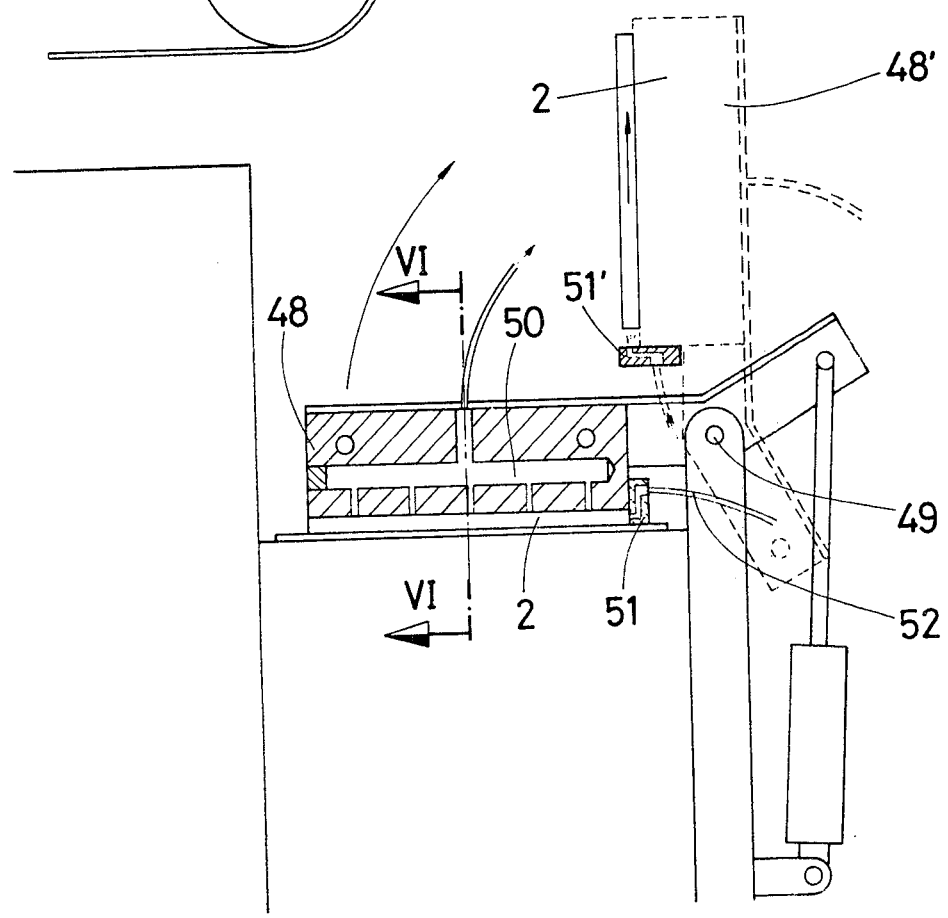

SAMPLING APPARATUS FOR A PRODUCTION LINE

The present invention relates to sampling apparatus for the automatic removal of a sample from a production line. The apparatus is particularly designed for sampling filter or cigarettes for the purpose of checking.

During the manufacture of filters for cigarettes, it is necessary to carry out frequent checks of the various parameters of the filter, in particular its pressure drop and its density, in order to limit waste and to remedy defects, in particular by a suitable adjustment of the machines.

Since the filters are manufactured in the form of a continuous rod containing cellulose acetate possibly combined with other filtering components, the ideal solution would be to check this rod directly and in a continuous manner. Apparatus has been proposed for this purpose. One of the latter is described in Swiss Pat. No. 576 242. The optical check carried out is nevertheless limited as regards the information obtained, which in practice is limited to detecting the presence or absence of the product in the filter rod.

It has also been proposed to carry out this check on the channelled guide drum receiving the small rods cut from the continuous rod at the outlet of the rod-forming arrangement. The possibilities of measuring the parameters of density and pressure drop on the guide drum are nevertheless very limited as regards their accuracy.

It has already been proposed to remove samples of cigarettes from a conveyor belt by means of a rotary arm connected to a source of vacuum for the purpose of subjecting them to an operation for checking their weight (U.S. Pat. No. 2,256,598). The arm moves above the stream of cigarettes in the direction of movement of this stream. The sample to be removed must be sucked with a relatively great force since the suction slot remains at a certain distance from this sample. This device does not make it possible to undertake any other check, in particular checking the pressure drop and density of the sample.

In order to carry out a precise check it was hitherto necessary to remove a filter rod manually in order to check the latter at a measuring station.

According to the present invention there is provided apparatus for the automatic removal of a sample from a production line comprising a rotary removal arm connected to a vacuum source, which the removal arm is provided with a concave rounded edge forming an abutment for the samples to be removed, at least one tubular member intended to receive the sample removed, means for driving the removal arm in an oscillating movement between a first removal position and at least one second position in which the sample is placed opposite the tubular transfer member, and means for introducing the sample into the tubular transfer member, said concave rounded edge serving to guide the sample at the time of this latter introduction.

The present invention intends to ensure automatic removal of filter rods after they leave the rod-forming arrangement, on the conveyor belt, for the purpose of automatic checking of their parameters and in this operation movements are kept to a minimum, which is an important factor in view of the fact that the operations are controlled pneumatically and in view of the inertia of the moving parts. It is advantageous to eliminate any waiting points or any intermediate storage.

In the present invention the removal arm preferably pivots about a horizontal spindle and the tubular transfer member is preferably constituted by a diametral bore in a vertical disc. Checking the pressure drop of the filter may be carried out in the disc, in a predetermined angular position of the disc. After such a check, if the latter is positive, the filter rod may be returned to the transfer arm in order to be re-introduced into the production line. A system of this type makes it possible to carry out checks at a very high frequency with a minimum amount of waste. The filter rod may also be sent from the disc to a checking station, either by means of another disc, or by means of the same disc, in another angular position of the latter.

The accompanying drawings show, by way of example, several embodiments of the apparatus according to the invention.

FIG. 5 is a front sectional view of a third embodiment.

FIG. 6 is a sectional view on line VI—VI of FIG. 5 also showing the guide drum diagrammatically.

Figure 1:
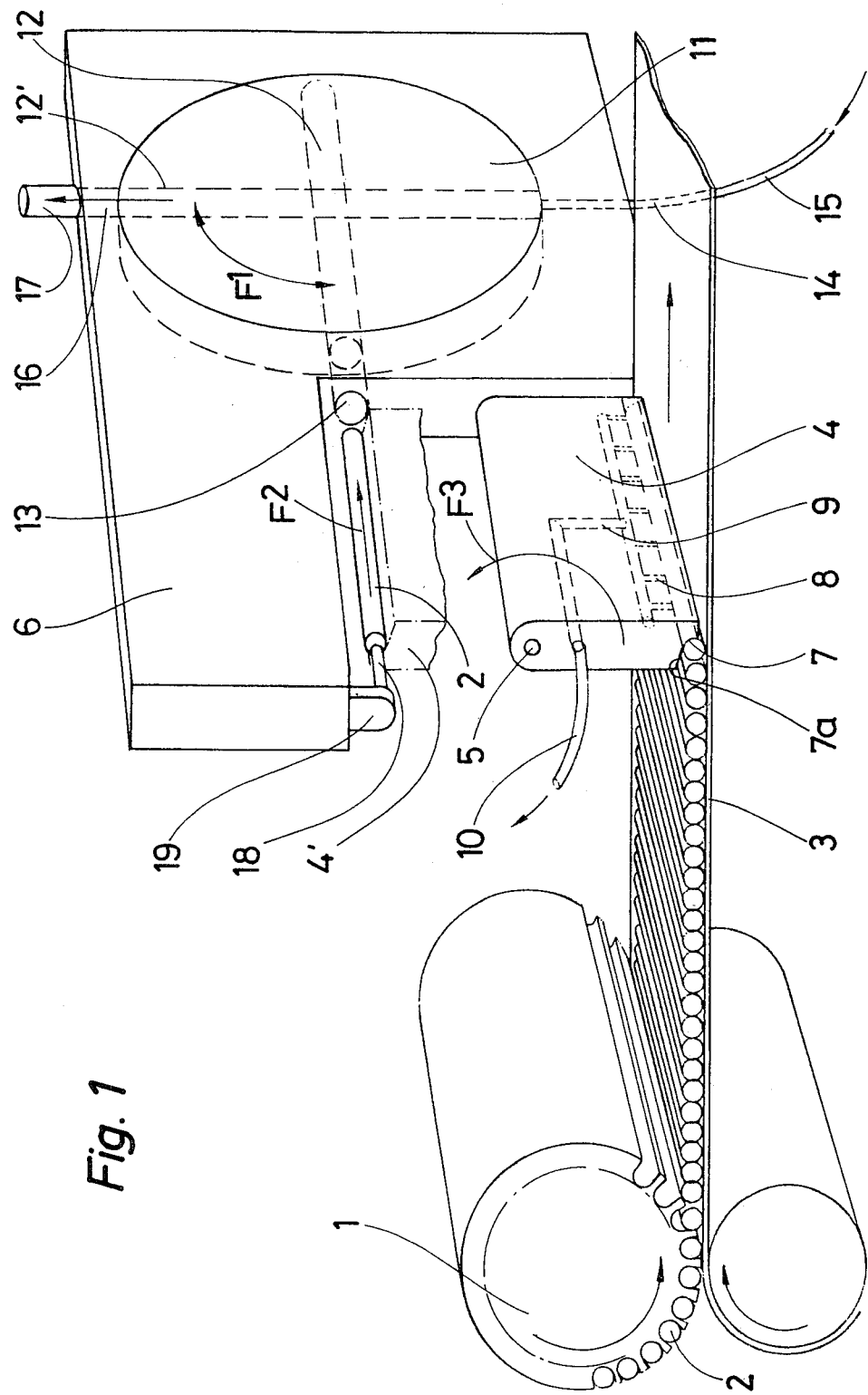
FIG. 1 is a perspective view in elevation of a first embodiment.

FIG. 1 shows diagrammatically a channelled guide drum 1, known per se, receiving the filter rods 2 after they have been cut from the rod formed continuously in the rod-forming device. The individual rods 2 are held by suction during part of the rotation of the drum 1 and are then subsequently deposited on a conveyor belt 3 which conveys them to a treatment station.

The removal device essentially comprises a removal arm 4 constituted by a plate of general rectangular shape mounted to pivot about a horizontal spindle 5 parallel to the rod 2. The removal arm 4 is mounted on a vertical frame 6 which supports pneumatic means (not shown) for setting the arm 4 in rotation. The horizontal lower edge of the removal arm 4 has a rounded concave part 7 whereof the bottom has an appropriate section in the shape of a quarter of a circle, one end of which is perpendicular to the conveyor belt 3, whereas the upper edge 7a is slightly oblique in the upwards direction, in order to facilitate the engagement of the rods 2 at the bottom of the rounded part 7. The surface 7 is connected by orifices 8 and a conduit 9 to a flexible pipe 10 connected to a source of vacuum. Mounted within the frame 6 is a circular rotary disc 11 able to move, by means of conventional pneumatic means (not shown), between two positions separated by an angle of 90°, as shown by the arrow F1. This disc is provided with a diametral hole 12 connected, in the horizontal position, to a hole 13 of the same diameter provided in the frame 6. In the vertical position 12', the bore 12 is connected at its lower end by a hole 14 to a pipe 15 connected to a source of compressed air and by its upper end through a hole 16 in the frame and a connector 17 to a pipe which is not shown and leads to a station for checking the filters. The frame 6 also comprises a push-rod 18 mounted on a support 19 integral with a pneumatic jack (not shown) for moving the push-rod in the direction of arrow F2. The various moving parts are all actuated pneumatically and controlled by a conventional control station.

The apparatus operates as follows: when a filter is to be removed, the removal arm 4 is lowered into the vertical position illustrated in full line. Its rounded edge 7 comes to bear on a rod 2 which is held in the latter by vacuum. The arm 4 pivots immediately through 180° in the direction of arrow F3 in order to occupy the position 4' shown in dot dash line. The arrival in this position initiates the forwards movement of the push-rod 18 which introduces the filter rod 2 through the hole 13 into the bore 12 in the disc 11. The arrival of the push-rod 18 in its end of travel position intiates the rotation of the disc 11 through 90°. The filter rod is then expelled immediately to the checking station by the compressed air entering at 15.

Figure 2:
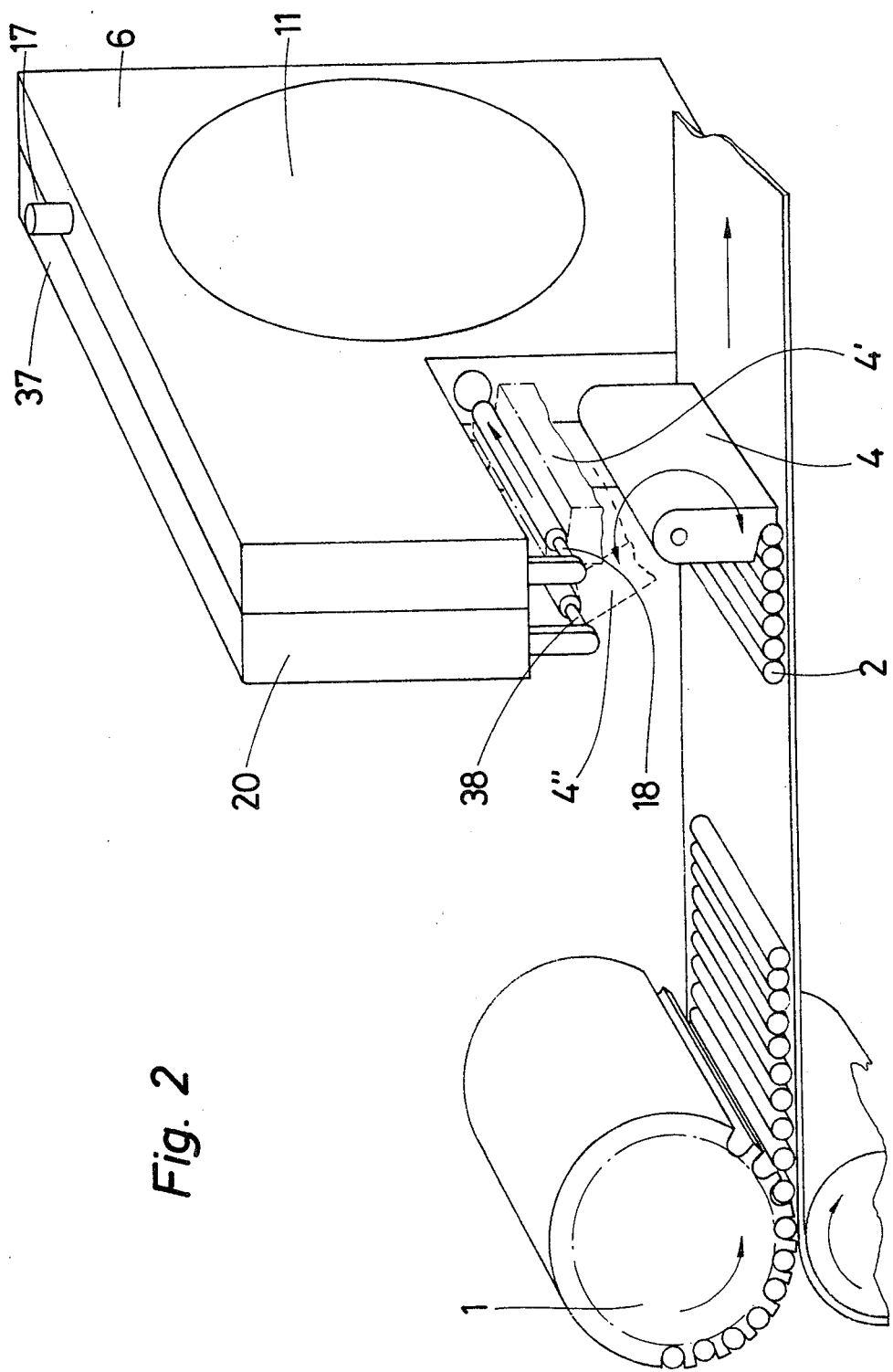
FIG. 2 is a perspective view of a second embodiment.
Figure 3:
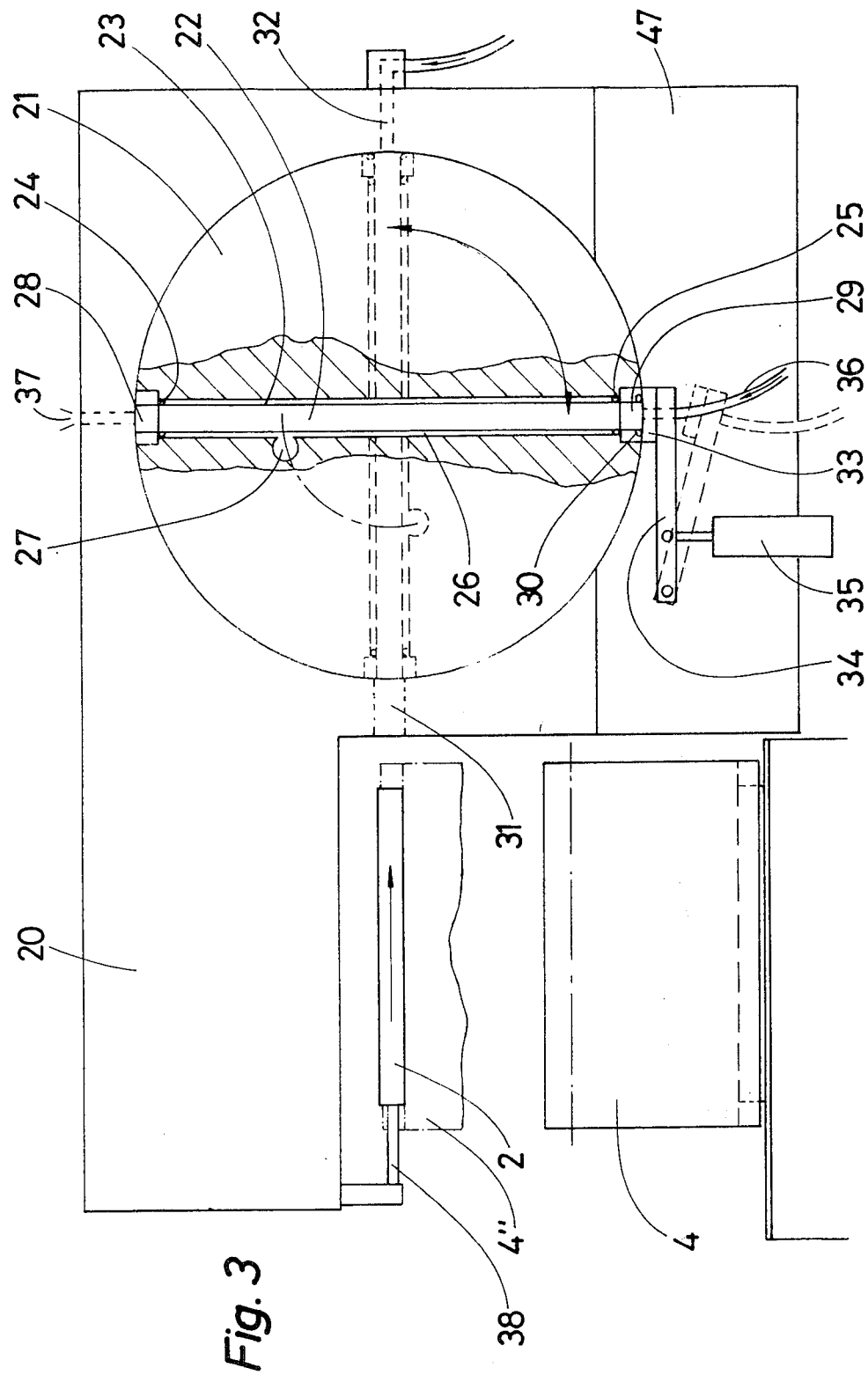
FIG. 3 is a front elevational view of part of the embodiment according to FIG. 2.

The second embodiment illustrated in FIGS. 2 and 3 differs solely from the first embodiment by the addition of a second frame 20, identical to the frame 6 and attached to the latter. This frame 20 also comprises a rotary disc 21, coaxial with the disc 11 and which is also provided with a diametral bore 22 in which is mounted a metal tube 23 open at both its ends and the wall of which is perforated. This tube 23 is lined internally with a rubber sleeve, the ends of which are rolled up in order to form two annular flanges 24 and 25 around the ends of the perforated tube 23, closing off the ends of the annular chamber 26 formed around the tube 23 in the manner of a gasket. This annular chamber 26 is connected by a hole 27 at right angles to the plane of the disc to a flexible pipe which is not shown and is connected to a pneumatic device which is able to create either excess pressure or reduced pressure. The tube 23 is retained in the bore 22 by two nuts 28 and 29. The nut 29 is also provided with an O-ring seal 30 which is flush with the periphery of the disc 21. Like the disc 11, the disc 21 is able to oscillate between two positions separated by an angle of 90°. In one of these positions the tube 23, in the horizontal position, is connected by one of its ends to a horizontal hole 31 in the frame and by its other end to a hole 32 connected to a source of compressed air. In the second position of the disc 21, the tube 23 is connected by its lower end to a valve 33 mounted at the end of a pivoted arm 34 in a recess 47 of the frame 20, below the disc 21 and actuated by a pneumatic jack 35 and provided with a central hole connected by a flexible pipe 36 to a source of slightly compressed air and having a constant rate of flow and by its other end to a calibrated discharge orifice 37. The frame 20 also comprises a push-rod 38 identical to the push-rod 18.

The apparatus operates in the following manner: if one intends to measure the pressure drop of the filter rod, the removal arm 4 pivots beyond the position 4' and stops in the position 4" in order to bring the filter rod 2 opposite the hole 31. The rod 2 is thus introduced by the push-rod 38 into the tube 23. Excess pressure in the chamber 26 holds the sleeve tightly around the rod in order to keep it in the tube. The disc 26 then pivots through 90° in order to reach the position shown in full line in the drawing. Simultaneously, the valve 33 bears against the end 29. Measuring the pressure drop is thus carried out conventionally. The disc 21 then returns to its initial position in which the sleeve is removed from the rod by vacuum and the rod is expelled from the tube 23 by compressed air arriving at 32 in order to be received by the removal arm 4 which returns it to the production line. It is thus possible to proceed with measuring operations at a high frequency and without any waste.

Instead of having two frames 6 and 20 and two discs 11 and 21, it is quite possible to provide a single frame and a single disc provided with two parallel bores.

Figure 4:
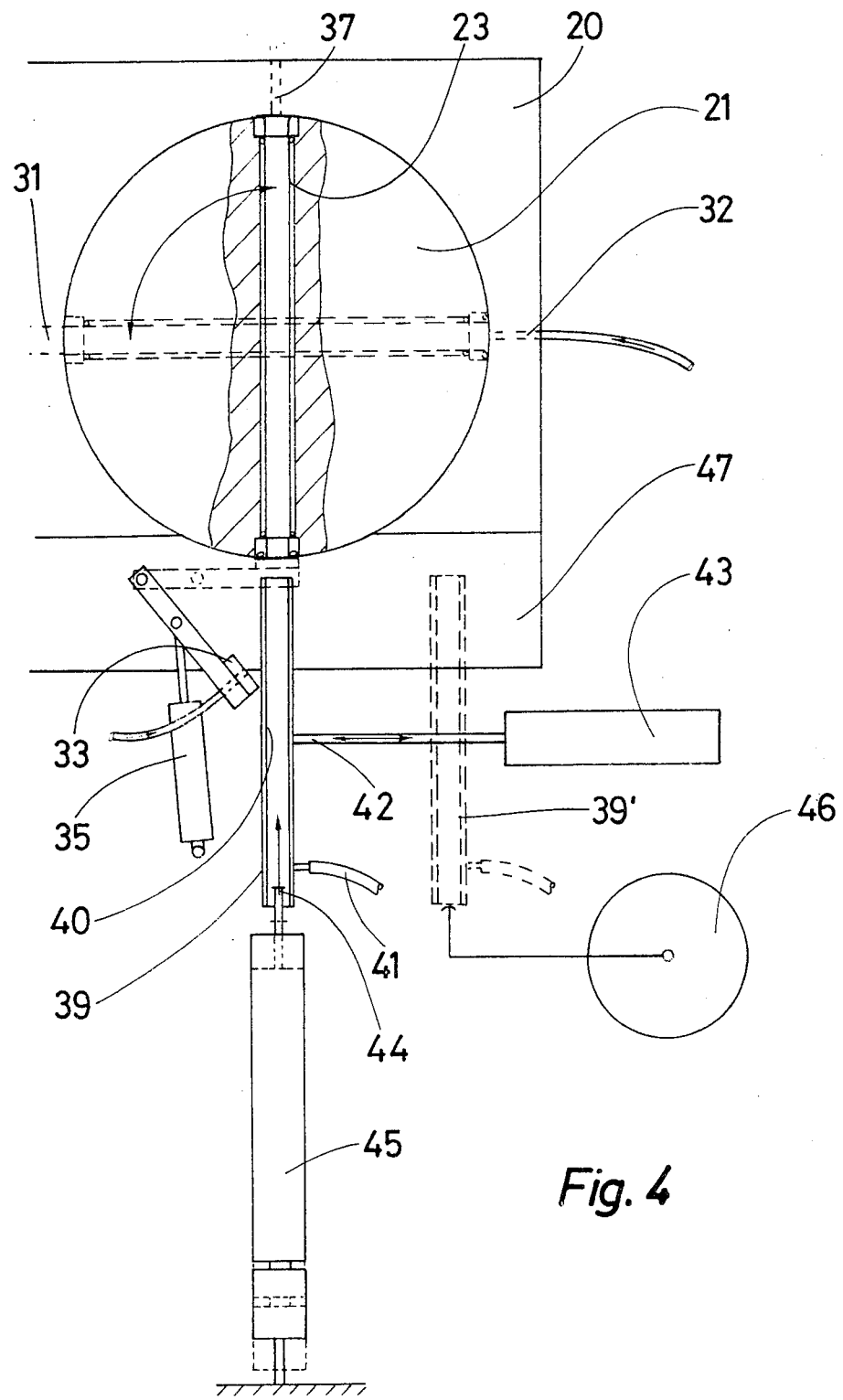
FIG. 4 is a view similar to FIG. 3 with an additional weighing device.

FIG. 4 shows diagrammatically a device for measuring the weight of the filter rod associated with the second embodiment. This device comprises a metal tube 39 which is open at its two ends and is provided with an internal rubber sleeve 40 and is connected by a flexible pipe 41 to a pneumatic device which makes it possible to create either excess pressure or reduced pressure between the tube and the sleeve. The tube 39 is fixed to the end of a horizontal arm 42 integral with the piston of a pneumatic jack 43. An abutment 44 which can be retracted by means of a jack 45 is able to engage in the tube 39. The weight is measured by means of a force pick-up illustrated diagrammatically at 46.

The apparatus operates in the following manner: the tube 23, containing the filter rod, is brought into the vertical position and the valve 33 is moved away, the rod is released so that it is able to fall freely into the tube 39 brought into a position forming an extension of the tube 23. As it falls in the tube 39 the filter rod is retained by the abutment 44. It is then held tightly by the sleeve 40 and the abutment 44 is retracted. The tube 39 is then moved by the jack 43 into the position 39'. The sleeve 40 releases the rod so that the weight of the latter can be measured by the force pick-up 46. The tube 39 is then moved towards the left and allows the filter rod to fall. It would also be possible to reintroduce the rod into the tube 23 of the disc 21 by pushing it by mechanical or pneumatic means. It is also possible to use a stationary abutment 44 which does not penetrate the tube 39.

The number of discs is not limited to two, but it would be possible to provide at least a third disc similar to the discs 11 and 21, for another check or another operation. Instead of using several discs or a single disc provided with several parallel diametral holes, it would also be possible to use a single disc provided with a single diametral hole and means for positioning the disc in several angular positions corresponding to different checks or operations. For example one could provide a first position at 45° for the discharge of the rod to a checking station, a second position at 90° for checking the weight and a third position as 135° for checking the pressure drop.

In the embodiment illustrated in FIGS. 5 and 6, the removal arm 48 is mounted to pivot about a spindle 49 parallel to the trajectory of the rods 2, adjacent the conveyor belt 3. The arm 48 also comprises a vacuum chamber 50 for gripping the rods 2. The end of the arm 48 close to the spindle 49 is provided with an ejection blower 51 connected by a flexible pipe 52 to a source of compressed air. After having gripped a rod, the arm 48 tilts into the vertical position 48' and the blower 51 drives the rod 2 into a tube 53 connected to a flexible pipe 54 and provided with a valve 55 which closes off the lower end of the tube 53 after the introduction of the rod 2, this valve 55 being provided with a blower 56 for sending the rod to a checking station through the pipe 54.

The apparatus according to the invention may also be used for checking cigarettes.

What is claimed is:

1. Apparatus for the automatic removal of a sample from a production line comprising a rotary removal arm connected to a vacuum source, the removal arm being provided with a concave rounded edge forming an abutment for the samples to be removed, at least one tubular member intended to receive the sample removed, means for driving the removal arm in an oscillating movement between a first removal position and at least one second position in which the sample is placed opposite the tubular transfer member, means for introducing the sample into the tubular transfer member, said concave rounded edge serving to guide the sample at the time of this latter introduction, the removal arm being mounted to pivot about a spindle parallel to its concave edge, and the tubular transfer member being constituted by a diametral bore in a rotary disc oscillating between a first horizontal position in which the sample is introduced into said bore and a second transfer and/or checking position.

2. Apparatus as claimed in claim 1, which comprises two parallel vertical oscillating discs, each provided with a diametral bore, mounted in at least one frame, the bore in the first disc being connected, in its second position, at one of its ends to a compressed air inlet and at the other end to a conduit for the discharge of the sample to a checking station, the bore in the second disc containing pneumatic means for the radial retention of the sample and being connected, in its second position, at one of its ends to a controlled source of compressed air and at the other end to an escape hole, for the purpose of checking the pressure drop of the sample.

3. Apparatus as claimed in claim 2, in which in its first horizontal position, the bore in the second disc is connected by its end remote from the inlet for the sample, to an intermittent source of compressed air for ejecting the sample in the direction of the removal arm, after the return of the disc to its first position, for reintroducing the sample back into the production line.

4. Apparatus as claimed in claim 3, in which the bore in the second disc is connected laterally to an intermittent source of compressed air and contains a perforated tube surrounding a short resilient sleeve whereof the bent ends form a gasket at the ends of the annular chamber formed between the tube and the diametral bore.

5. Apparatus as claimed in claim 2 or 3, in which the frame in which the second disc is mounted supports a movable support to which is fixed the end of a conduit connected to the controlled source of compressed air for checking the pressure drop, thus making it possible to apply the controlled source of compressed air to the end of the bore or to move it away therefrom.

6. Apparatus as claimed in claim 5, in which the bore in the second disc is in a vertical position in the second position of the disc and the apparatus also comprises a vertical tube open at its ends which tube is intended to receive a sample and is able to move between a first position in which it forms an extension of the bore in the second disc in the vertical position and is above an axial abutment and a second position in which it is above a balance, said tube comprising means for retaining the sample radially as it is transferred from the first to the second position.

7. Apparatus for the automatic removal of a sample from a production line comprising a rotary removal arm connected to a vacuum source, the removal arm being provided with a concave rounded edge forming an abutment for the samples to be removed, at least one tubular member intended to receive the sample removed, means for driving the removal arm in an oscillating movement between a first removal position and at least one second position in which the sample is placed opposite the tubular transfer member, means for introducing the sample into the tubular transfer member, said concave rounded edge serving to guide the sample at the time of this latter introduction, the removal arm being mounted to pivot about a horizontal spindle perpendicular to the plane containing its concave edge and being provided at one end with a blower device directed along the axis of the concave edge and in which the tubular transfer member being provided with a closure valve connected to a source of compressed air and whereof the outlet being connected to a discharge conduit leading to a checking station.

8. Apparatus as claimed in claim 7, in which the removal arm is constituted by a plate of rectangular shape and the concave portion of the edge of the removal arm comprises a section at least approximately in the shape of a quadrant and whereof the ends are respectively perpendicular to the edge and one side of the arm.

9. Apparatus as claimed in claim 1, in which the rotary disc can occupy at least three angular positions, a first in which the sample is discharged to a checking station, a second in which the pressure drop of the sample is measured directly and a third in which the weight of the sample is measured.

* * * * *